United States Patent [19]

Wade et al.

[11] Patent Number: 5,632,995

[45] Date of Patent: May 27, 1997

[54] METHOD FOR STIMULATION OF REPRODUCTIVE PERFORMANCE

[75] Inventors: Jose M. Wade, Celbridge, Ireland; Stanley J. Alkemade, Seaforth, Canada

[73] Assignee: Vetrepharm, Inc., Canada

[21] Appl. No.: 416,061

[22] Filed: Apr. 4, 1995

Related U.S. Application Data

[63] Continuation of Ser. No. 112,602, Aug. 27, 1993, abandoned.

[51] Int. Cl.$^6$ .......................... A61K 39/04; A61K 35/74
[52] U.S. Cl. ...................... 424/282.1; 424/278.1; 424/248.1; 424/195.1
[58] Field of Search .................. 424/248.1, 278.1, 424/282.1, 93.4, 520, 195.1

[56] References Cited

U.S. PATENT DOCUMENTS

| | | | |
|---|---|---|---|
| 3,172,815 | 3/1965 | Fox et al. | 424/282.1 |
| 4,340,586 | 7/1982 | Bekierkunst | 424/282.1 |
| 4,503,048 | 3/1985 | Cantrell | 424/195.1 |
| 4,744,984 | 5/1988 | Ragland | 424/282.1 |
| 5,006,334 | 4/1991 | Stevens | 424/195.1 |

FOREIGN PATENT DOCUMENTS

| | | |
|---|---|---|
| 2 020 758 | 7/1970 | France . |
| 2 719 547 | 11/1977 | Germany . |
| 2 756 851 | 6/1978 | Germany . |
| 3 434 766 | 4/1986 | Germany . |
| WO 87/02249 | 4/1987 | WIPO . |
| WO 91/18617 | 12/1991 | WIPO . |

OTHER PUBLICATIONS

Szekeres Bartho et al., American Journal of Reproductive Immunology 26(2): 82–83 (1991).
Toder et al., American Journal of Reproductive Immunology 26(1): 42 46 (1991).
Toder et al., American Journal of Reproductive Immunology 24(3): 63–66 (1990).
Toder et al., Journal of Reproductive Fertility Supplement 37: 79–84 (1989).
Espey, L.L., "Ovulation as an Inflamamatory Reation—A Hypothesis," *Biology of Reproduction*, vol. 22, No. 1, pp. 73–106 (Feb. 1980).
Sjögren, A. et al., "Interleukin–1a modulates luteinizing hormone stimulated cyclic AMP and progesterone release from human granulosa cells in vitro," *Human Reproduction*, vol. 6, No. 7, pp. 910–913 (1991).
Stewart, C.L. et al., "Blastocyst implantation depends on material expression of leukaemia inhibitory factor," *Nature*, vol. 359, pp. 76–79 (Sep. 3, 1992).
Chaouat, G.et al., "Control of fetal survival in CBA×DBA/2 mice by lymphokine therapy," *Journal of Reproduction & Fertility*, vol. 89, pp. 447–458 (1990).
Mogil, R.J. et al., "Maternal Immune Reactivity as a Determinant of Placental Function and Fetal Survival," *Seminars in Reproductive Endocrinolgy*, vol. 6, No. 2, pp. 145–154 (May 1988).
Seamark, R.F et al., "Influence of the immune system on reproductive function," *Animal Reproduction Science*, vol. 28, pp. 171–178 (1992).
Finn, C.A., "Implantation, Menstruation and Inflammation," *Biology Review*, vol. 61, pp. 313–328 (1986).
Debnath, J.C., et al., "Enhanced production of antibidy with specific antigen," *Chemical Abstracts*, col. 117, No. 1, p. 48, No. 502z (1992); *Indian J. Exp. Biol.*, vol. 30, No. 2, pp. 73–76 (1992).
Mallick, B.B., et al., "Induction of CMI response by muramyl dipeptide and comparison with that of nonspecific stimulator of immunity,"*Chemical Abstracts*, vol. 105, No. 13, p. 38, No. 108 148e (1986); *Aspects Allergy Appl. Immunol.*, vol. 18, pp. 65–71 (1985).

*Primary Examiner*—Jean C. Witz
*Attorney, Agent, or Firm*—Jones & Askew

[57] ABSTRACT

The present invention relates to an immunostimulant composition and method of use that is effective for increasing reproductive performance in an animal or human. More particularly, the present invention is the use of a mycobacterial cell wall preparation for stimulating the immune system of an animal or human in such a way as to cause an increase in reproductive performance of the animal or human.

5 Claims, 1 Drawing Sheet

METHOD FOR STIMULATION OF REPRODUCTIVE PERFORMANCE

This is a continuation of application Ser. No. 08,112,602, filed Aug. 27, 1993 now abandoned.

TECHNICAL FIELD

The present invention relates to an immunostimulant composition and method of use that is effective for increasing reproductive performance in animals and humans. More particularly, the present invention is the use of a bacterial cell wall preparation for stimulating the immune system of an animal or human in such a way as to cause an increase in reproductive performance of the animal or human.

BACKGROUND OF THE INVENTION

As used herein, the term "immunostimulant" means a composition which is capable of stimulating a non-specific immune response in an animal or human. As used herein, "reproductive performance" means an increase in number of offspring, an increase in survival rate of offspring, an increase in first service conception rate and a decrease in service number per conception. As used herein, "apparently infertile" means infertility diagnosed by the clinical criteria applicable to a particular species of animal or to a human.

The immune response involves the whole body and is modulated and affected by many complex interactions. Non-specific immune stimulation is capable of accelerating and amplifying many immune responses. Immunostimulants of bacterial, yeast, viral, plant, chemical and biotechnological origin may be used to non-specifically stimulate immune activity. Immunostimulants derived from Mycobacteriacae and Actinomycetaceae including Mycobacterium, Corynebacterium (Proprionebacterium), Nocardia, Rhodococcus, other Coryneform bacteria, Bordetella, Listeria, and bacille Calmette-Guerin (BCG) have been used to non-specifically stimulate immune activity.

Two components relevant to non-specific immunostimulant activity have been identified and isolated from the bacille Calmette-Guerin (BCG). N-Acetyl-muramyl-alanyl-3-isoglutamine (muramyl dipeptide) is a small component of the mycobacterial cell wall that can mediate the immunostimulant activity produced by whole mycobacteria in the water-in-oil emulsion of Freund's complete adjuvant. Muramyl dipeptide can activate macrophages and potentiate T-and B-cell-mediated reactions. Trehalose dimycolate is another component of mycobacteria that has immunostimulant activity.

Whether large complex molecules like peptidoglycans and lipopolysaccharides or simple molecules such as muramyl dipeptide and trehalose dimycolate are used, the common pathway points to macrophage and monocyte activation as the mechanism of immunostimulant activity. Activation of macrophages and monocytes results in increased synthesis and release of bioactive proteins and lipids which initiate, accelerate and amplify the immune response.

The non-specific immunostimulant activity of preparations from microorganisms has been studied extensively. Bacterial cell wall extracts have been used to treat diseases of the skin (U.S. Pat. No. 4,340,586), bacterial infections (U.S. Pat. No. 3,172,815), tumors (U.S. Pat. No. 4,503,048), and virus infections (U.S. Pat. No. 4,744,984) in animals and humans. Immune stimulation has been used in contraception and abortion (U.S. Pat. No. 5,006,334).

Reproductive performance is of great importance in enterprises where the breeding of animals is necessary for the commercial success of the enterprise. Reproductive performance also is of great importance to humans attempting to conceive a child. Attempts to increase reproductive performance have largely focused on the use of reproductive hormones to manipulate reproductive performance. These attempts include, but are not limited to, stimulation of reproductive hormone synthesis and secretion, induction of ovulation and/or superovulation using purified and/or synthetic hormones, artificial insemination and, more recently, the use of in vitro fertilization and embryo transfer techniques. These methodologies have provided various degrees of success in increasing reproductive performance in different species. Each of these methodologies, however, is labor intensive and requires sophisticated and expensive technologies for its implementation.

Immune cells respond to the cyclically changing hormonal environment within reproductive tissues so that major events such as ovulation, implantation and parturition resemble an inflammatory and reparative response to infection. Likewise, reproductive tissues respond to bioactive proteins and lipids produced by immune cells so that a complex of interactions among neuroendocrine hormones, macrophages, fibroblasts, reproductive tissue cells and other cells participate in the coordination of reproduction.

For example, ovulation can be described as an immune inflammatory reaction (Epsey, L.L., 1980, Ovulation As An Inflammatory Reaction-A Hypothesis, *Biol. Reprod.* 22:73–106). Inflammatory exudates containing mitogenic factors may stimulate DNA synthesis and cell division in quiescent follicles (Epsey, L. L., 1980, Ovulation As An Inflammatory Reaction-A Hypothesis, *Biol. Reprod.* 22:73–106). Interleukins may increase the expression of luteinizing hormone (LH) receptors on mature follicles and may sensitize follicles to LH thereby increasing ovulatory rates. Further, interleukins may have a regulatory role in the transition of granulosa cell to luteal cells in the ovary (Sjogren et al., 1991, Interleukin-1a Modulates Luteinizing Hormone Stimulated Cyclic AMP and Progesterone Release From Human Granulosa Cells In Vitro, *Human Reprod.* 6:910–913). Interleukins also may sensitize testicular Leydig cells to luteinizing hormone and increase spermatogenesis.

Implantation also can be described as an immune inflammatory response (Finn, C. A., 1986, Implantation, Menstruation and Inflammation, *Biol. Rev.* 61:3213–28). Oestrogen and progesterone regulate the expression of leukemia inhibitory factor and cytokines by uterine epithelial cells and both leukemia inhibitory factor and cytokines are necessary for zygote implantation (Stewart et al., 1992, Blastocyte Implantation Depends on Maternal Expression of Leukemia Inhibitory Factor, *Nature* 359:76–79). Cytokines also may be embryotrophic factors which enhance communication between the developing embryo and the mother (Mogil et at., 1988, Maternal Immune Reactivity as a Determinant of Placental Function and Fetal Survival, *Sem. Reprod. Endocrinol.* 6:145–154). In fact, insufficient production of cytokines has been implicated in increased embryonic death (Chaouat et at., 1990, Control of Fetal Survival in CBA-X DBA/2 Mice by Lymphokine Therapy, *J. Reprod. Fertil.* 89:447–458). Cytokines also may play a major role in the inflammatory events of parturition and postnatal repair.

Thus, what is needed is a composition and method of use that is effective for stimulating the immune system of an animal or human in such as way as to increase the reproductive performance of the animal or human.

SUMMARY OF THE INVENTION

The present invention provides an immunostimulant composition and method of use for non-specifically stimulating the immune system of an animal or human in such a way as to increase the reproductive performance of the animal or human. Non-specific stimulation of the immune system may, but does not necessarily, initiate interactions among neuroendocrine hormones, macrophages, fibroblasts and other cells within the reproductive tract which increase reproductive performance.

The immunostimulant used to increase reproductive performance in an animal or human according to the present invention comprises a modified bacterial cell wall extract (CWE) from a nonpathogenic bacterium. Administration of a suspension of CWE to an animal or human causes the immune system of the animal or human to be non-specifically stimulated in such a way as to cause an increase in reproductive performance of the animal or human. This may result from, but is not limited to, an increase in mating rate, an increase in ovulation rate, an increase in implantation rate, an increase in parturition rate, and an increase in pregnancies per year in the female, and an increase in spermatogenesis, an increase in sperm motility and an increase in sperm viability in the male. Thus, reproductive performance, as measured by an increase in number of offspring, an increase in survival rate of offspring, an increase in first service conception rate and a decrease in service number per conception is enhanced.

The effectiveness of CWE to non-specifically stimulate the immune system of an animal or human in such a way as to increase reproductive performance in an infertile, subfertile or fertile animal or human is completely unexpected. The use of CWE to increase reproductive performance in an animal or human is different from previous methods for increasing reproductive performance in an animal or human and is different from previous uses of CWE.

Accordingly, it is an object of the present invention to provide a composition and method of use of an immunostimulant to stimulate the immune system of an animal or human in such a way as to increase reproductive performance in the animal or human.

It is a further object of the present invention to provide an immunostimulant that is effective in increasing reproductive performance in an apparently infertile animal or human.

It is a further object of the present invention to provide an immunostimulant that is effective in increasing reproductive performance in a sub-fertile animal or human.

It is a further object of the present invention to provide an immunostimulant that is effective in increasing reproductive performance in a fertile animal or human.

It is a further object of the present invention to provide an immunostimulant that is effective in increasing reproductive performance in a female animal or human.

It is a further object of the present invention to provide an immunostimulant that is effective in increasing reproductive performance in a male animal or human.

It is a further object of the present invention to provide an immunostimulant that is effective in increasing the mating rate of a group of animals or humans.

It is a further object of the present invention to provide an immunostimulant that is effective in increasing the first service conception rate of an animal or human.

It is a further object of the present invention to provide an immunostimulant that is effective in decreasing service number per conception of an animal or human.

It is a further object of the present invention to provide an immunostimulant that is effective in increasing pregnancy number per year in a female animal or human.

It is a further object of the present invention to provide an immunostimulant that is effective in increasing the number of mature follicles per ovulatory cycle in a female animal or human.

It is a further object of the present invention to provide an immunostimulant that is effective in increasing conception rate in a female animal or human.

It is a further object of the present invention to provide an immunostimulant that is effective in increasing zygote implantation in a female animal or human.

It is a further object of the present invention to provide an immunostimulant that is effective in increasing parturition in a female animal or human.

It is a further object of the present invention to provide an immunostimulant that is effective in increasing the number of live offspring of an animal or human.

It is a further object of the present invention to provide an immunostimulant that is effective in increasing the survival rate of offspring of an animal or human.

It is a further object of the present invention to provide an immunostimulant that is effective in increasing spermatogenesis in a male animal or human.

It is a further object of the present invention to provide an immunostimulant that is effective in increasing motility of sperm in a male animal or human.

It is a further object of the present invention to provide an immunostimulant that is effective in increasing viability of sperm in a male animal or human.

It is a further object of the present invention to provide a bacterial cell wall extract that is effective in stimulating the immune system of an animal or human in such as way as to increase reproductive performance of the animal or human.

It is a further object of the present invention to provide a mycobacterial cell wall extract that is effective in stimulating the immune system of an animal or human in such as way as to increase reproductive performance of the animal or human.

These and other objects, features and advantages of the present invention will become apparent after a review of the following detailed description of the disclosed embodiment and the appended claims.

DETAILED DESCRIPTION OF THE DISCLOSED EMBODIMENT

Figure 1A:
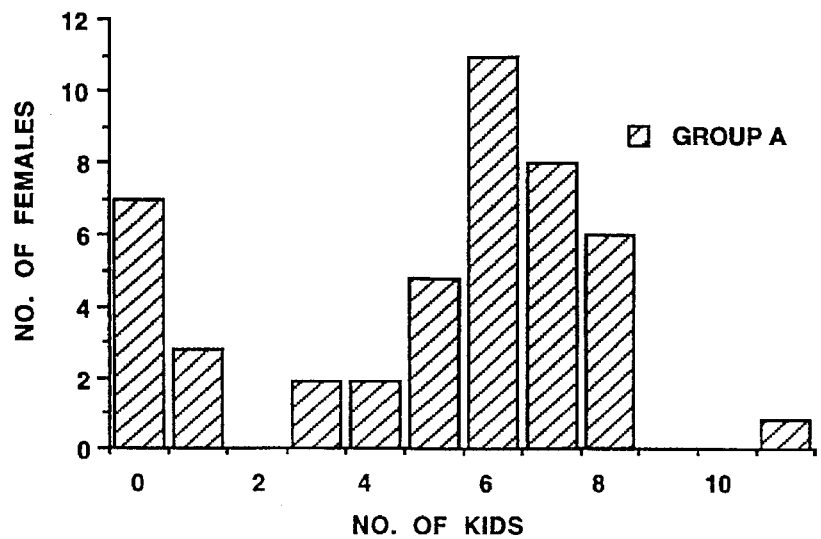
FIGS. 1A–1C show a distribution of litter sizes among treatments.

The present invention relates to the use of an immunostimulant composition to stimulate the immune system of an animal or human in such a way as to increase reproductive performance of the animal or human. The immunostimulant for use in the present invention is a preparation of bacterial cell wall that is capable of stimulating the immune system of an animal or human in such a way as to cause an increase in reproductive performance of the animal or human.

It is to be understood that the present invention is not an immunization process but is an immunostimulant process whereby the immune system of an animal or human is stimulated in such a way that the individual's own immune system is capable of increasing reproductive performance.

Thus, the immunostimulant composition and method of use of the present invention is ideally suited for increasing reproductive performance in apparently infertile, in sub-fertile and in fertile animals and humans.

The immunostimulant for use in the present invention may be of bacterial, yeast, viral, plant, biotechnological and chemical origin. Preferably, the immunostimulant is a preparation of bacterial cell wall and can be prepared from, but not limited to, Mycobacteriacae and Actinomycetaceae including, but not limited to, Mycobacterium, Corynebacterium (Proprionebacterium), Nocardia, Rhodococcus, other Coryneform bacteria, Bordetella, Listeria, and bacille Calmette-Guerin (BCG). More preferably, the immunostimulant is a modified cell wall extract (CWE) from a nonpathogenic Mycobacterium. Most preferably, the immunostimulant is a purified and deproteinized CWE from the *Mycobacterium phlei* (MCWE). Administration of an amount of MCWE to an animal or human, sufficient to non-specifically stimulate the immune system of the animal or human, is a novel and unexpected method for increasing reproductive performance of the animal or human.

Basically, the immunostimulant for use in the present invention is prepared by growing a microorganism, *Mycobacterium phlei* for example, in Bacto AC broth (Difco Labs, Detroit, Mich.) for 10 to 20 days after primary culture on Petragnani medium (Difco Labs, Detroit, Mich.) or in Lowenstein-Jensen medium (Difco Labs, Detroit, Mich.) for 10 to 20 days. The cells are harvested by centrifugal sedimentation and disrupted, either under pressure or by sonic disruption. Disruption of bacteria means breaking the bacterial cell walls so that the soluble contents of the bacteria are released into the surrounding milieu. The disrupted bacterial cells are collected by centrifugation and resuspended in distilled water. The cell/water suspension is first treated in a blender at high speed. The bacterial cells are further disrupted in a high pressure cell fractionator. The bacterial cells are placed in a chamber of a high pressure cell fractionator. The chamber is then pressurized to pressures greater than 30,000 pounds per square inch. The pressure is then rapidly released and the cells are disrupted by decompression. The bacterial cells may also be disrupted by sonication in a sonifier such as a Branson Sonifier 350 cell disrupter (Branson Sonic Power Co., Danbury, Conn.).

The cell wall fraction is then washed and separated from any unbroken cells. The effluent or sonicate is transferred to centrifuge bottles and is centrifuged at about 27,500× g for 1 hour at 15° C. in an intermediate speed centrifuge. After centrifugation, the supernatant solution is discarded and the sedimented crude cell wall fraction is transferred to a blender. It is important at this step to discard the undermost, white pellet of unbroken cells. The cell walls are suspended in deionized, sterile water and are washed by centrifugation. The washed cell wall fraction is resuspended in deionized, sterile water and spun at low speed (about 350 to 500× g) to remove any unbroken cells. After the low speed centrifugation, the cell wall fraction is pelleted from the supernatant solution by centrifugation at 27,500× g.

The crude cell wall fraction is then deproteinized by treating the cell walls with several proteinases. It is to be understood that many different proteinases, and even chemical extraction methods, can be used for this step in the cell wall modification process. The preferred method of deproteinating the cell walls is by sequential treatment of the cell wall fraction with trypsin and pronase. The crude cell wall fraction is resuspended in an aqueous buffered solution such as 0.05M Tris-HCl, pH 7.5. Trypsin (pancreatic trypsin, Sigma Chemical Co., St. Louis, Mo.) is added, and the mixture is stirred at room temperature for 6 to 24 hours. After the trypsin treatment, pronase (*Streptomyces griseus* protease, Sigma Chemical Co., St. Louis, Mo.) is added and the suspension is allowed to incubate at room temperature for 6 to 24 hours.

The cell wall fraction is then optionally treated with detergent and phenol to extract any nucleic acids and/or lipids that may be present in the cell wall fraction. The preferred extraction mixture is urea, Triton X-I00, and phenol. For example, between about 40 to 80 g of urea, 0.5 to 4 ml of 100% Triton X-I00, and 50 to 150 g of phenol are added to each liter of deproteinized cell wall suspension. The suspension is then warmed to about 60° to 80° C. and stirred for 1 hour. After the heating step with the phenol and detergents, the suspension is spun for 10 minutes at about 16,000× g in capped bottles in an intermediate speed centrifuge in a GSA rotor. The supernatant solution is decanted and the dark phenol solution under the pellet is carefully removed. The cell wall pellet is washed several more times by centrifugation to remove any residual phenol. Next the modified cell wall pellet is lyophilized, a process well known to those skilled in the art. The lyophilized cell wall pellet can be stored indefinitely at −20° C. in a desiccator jar.

The MCWE composition effective for increasing reproductive performance in an animal or human can be administered in an aqueous vehicle or in an adjuvant vehicle. Preferably, the MCWE is administered emulsified in an adjuvant vehicle. The adjuvant can be one of many adjuvants well known to those skilled in the art. The preferred adjuvant is an oil and water emulsion. The immunostimulant composition for use in the present invention is mixed with oil before aqueous buffer with detergent is added. The mixture is then emulsified by any one of several methods including, but not limited to, using a high speed blender, a sonicator, or a Potter-Elvehjem homogenizer. Numerous oil and aqueous components, their proportions, and methods for their emulsification are known to those skilled in the art and can be used to prepare the immunostimulant composition for use in practicing the present invention. The method of preparing the emulsion is not critical.

The preferred emulsion of deproteinized cell walls is prepared by addition of between approximately 5 and 15 g of dry, deproteinized mycobacterial cell wall to a sterile beaker. Mineral oil, synthetic mineral oil, n-hexadecane (Drakeol 6-VR, Penreco, Butler, Pa.) or squalene is added at between approximately 10 and 50 ml per gram of cell walls. The suspension is covered and is mixed for approximately 30 minutes to overnight. Between approximately 10 ml to 20 ml aliquots of the oil/cell wall mixture is transferred to a sterile 1 liter beaker. Sterile phosphate buffered saline containing a detergent, PBS-D (16.5 ml of 0.2M $NaH_2PO_4$, 33.5 ml of 0.2M $Na_2HPO_4$, 7.4 g NaCl, 2 ml Tween-80 diluted to 1 liter with deionized water) is added to a final volume of 500 ml. The mixture is emulsified by sonication using a Heat Systems Sonicator, XL2015 cell disruptor and by using a Microfluidics microfluidizer set at 90–100 p.s.i. (20,700–23,000 p.s.i. actual chamber pressure) The emulsion is transferred to sterile bottles and stored at 4° C.

Optionally, one or more preservatives and/or antibiotics can be added to the mixture prior to sonication. For example, thimerosol (Sigma Chemical Co., St. Louis, Mo.), and/or gentamicin (Sigma Chemical Co., St. Louis, Mo.) and or amphotericin (Sigma Chemical Co., St. Louis, Mo.) can be added. The preferred concentration of thimerosal is between about 0.005% to 0.015%, of gentamicin is between about 20 µg/ml and 40 µg/ml, and of amphotericin is 2.0 µg/ml to 3.0 µg/ml.

Optionally, aluminum hydroxide stabilizer may be added to the emulsion. Aluminum hydroxide is obtained as a 9.4% compressed gel from the Reheis Chemical Co. (Berkeley Heights, N.J.) and is hydrated to 1.3% aluminum oxide by the addition of deionized water. The gel is sterilized in an autoclave at 120° C. for 20 minutes before it is added to the cell wall emulsion. One ml of the final emulsion contains about 50 μl of 1.3% aluminum oxide.

Also, the MCWE composition effective for increasing reproductive performance can optionally contain glycosaminoglycans (GAGs) as a component. Examples include, but are not limited to, polysulfated GAGs, and salts of hyaluronic acids including sodium hyaluronate. The preferred glycosaminoglycan is hyaluronic acid, which is of rooster comb or streptococcal origin. The hyaluronic acid derived from streptococcus has a molecular weight range of 300,000 to 2,000,000 Daltons and a preferred range of 500,000 to 1,200,000 Daltons and a concentration range of 0.001% to 1.0% and a preferred range of 0.01% to 0.1%.

A summary of mycobacterial cell wall (MCW) production from *Mycobacterium phlei* is as follows:

1. Cell Growth
   a. Identify seed culture as pure *Mycobacterium phiei*.
   b. Inoculate broth media in Erlenmeyer flasks.
   c. Incubate 4–21 days at 35°–38° C.
2. Concentration of whole cells
   a. Centrifugation.
3. Washing of whole cells
   a. Repeated centrifugations in distilled water.
4. Inactivation and disruption of whole cells
   a. Ribi Cell Fractionator (or)
   b. Branson Sonicator (or)
   c. Heat Systems Sonifier.
5. Detoxification of disrupted cells
   a. Repeated centrifugations in deionized water.
6. Concentration of raw MCW
   a. Centrifugation.
7. Deproteinization of raw MCW
   a. Suspension in Tris-HCl, pH 7.3 to pH 7.7.
   b. Degradation in trypsin for 6–24 hours.
   c. Degradation in pronase for 6–24 hours.
   d. Optional incubation in urea/phenol for 1 hour.
8. Pasteurization at 60°–80° C. for 1 hour.
9. Concentration of deproteinized and purified MCW.
   a. Centrifugation.
10. Stabilization
    a. Lyophilization.
    b. Optional addition of preservatives and/or antibiotics.

The known active ingredients of the present invention, the family of muramyl dipeptides and trehalose dimycolate, as well as any unknown active components which may be present in the modified cell walls of bacteria, may be delivered to the host by any number of vehicles other than by the preferred oil in water emulsions. The MCWE for use in the present invention can be used with one, all, or any combination of ingredients regardless of the carrier-vehicle used to present them to the responsive immune cells. These include, but are not limited to, aqueous vehicles, liposomes, various biodegradable or nondegradable polymers, and osmotic minipumps.

The MCWE composition for use in the present invention can be administered orally, subcutaneously, intramuscularly, intravenously, transdermally, and by topical contact with mucous membranes including, among others, mucous membranes of the vagina, cervix and uterus. Preferably, the MCWE is administered intramuscularly, intravenously or orally. More preferably, the MCWE is administered intramuscularly or orally. Most preferably, the MCWE is administered intramuscularly to animals and orally to humans. The MCWE composition is administered preferably in a single treatment. However, it should be understood that more than one treatment may be necessary or desirable. The optimal dose of MCWE effective for increasing reproductive performance varies according to the immune system of the animal or human being treated. The dose is from about 0.0001 mg to about 10.0 mg of MCWE per ml of vehicle in a total volume of from about 0.001 ml to about 5.0 ml. Preferably, the dose is from about 0.001 mg to about 4.0 mg of MCWE per ml of vehicle in a total volume of from about 0.010 ml to about 3 ml.

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example I

*Mycobacterium phlei* are obtained from the Institut fur Experimental Biologic and Medizin, Borstel, Germany, and are stored as a suspension in sterile milk at −60° C. Approximately 11 transfers of the isolate were made between 1976 and 1985 without any diminution of immunostimulant activity of the modified cell walls. The *M. phlei* are cultured on Petragnani medium (Difco Labs, Detroit, Mich.).

Example II

Bacterial cell walls are prepared with a Ribi Cell Fractionator or with a Heat Systems Sonicator XL2015. The Ribi cylinder, piston, and valve components are cleaned and assembled before each use. Approximately 400 grams of moist cell mass are placed into a clean blender with a capacity of approximately 1200 ml. The cell mass is mixed at high speed for between 30 to 60 seconds. After mixing, 6 ml of Tween 80 and between 200 and 400 ml of sterile water are added to the cell mixture. The entire cell suspension is then mixed in the blender at low speed for about 10 seconds. The cell suspension is refrigerated and remixed before each refill of the Ribi cylinder. The Ribi cylinder is filled with the cell suspension and processed in the fractionator at 33,000 pounds per square inch. The cylinder is then refilled and the procedure is repeated until the entire cell suspension has been processed. The effluent from the Ribi cylinder is stored in a sterile flask on ice during the fractionation process.

Example III

The effluent from the fractionation procedure of Example II is transferred to 250 ml centrifuge bottles and spun for 1 hour at 27,500× g at 15° C. in an intermediate speed centrifuge with a GSA rotor. The supernatant fluid from the centrifugation is then decanted and discarded. The undermost, white pellet of unbroken cells is discarded. The sedimented crude cell wall fraction is transferred to a blender and suspended in sterile, deionized water by mixing at low speed. The crude cell wall fraction is washed by resuspension and centrifugation (27,500× g at 15° C. for one hour). Again, the undermost, white pellet of unbroken cells is discarded.

After washing the crude cell wall fraction, the pellet is resuspended in sterile, deionized water and spun for 5 minutes at 350× g to sediment unbroken cells while retaining the cell walls in the supernatant fluid. The supernatant fluid is then decanted and centrifuged at 27,500× g for 1 hour at 15° C. to sediment the crude cell wall fraction.

Example IV

The crude cell wall fraction from Example III is then deproteinized by digestion with proteolytic enzymes. The crude cell wall fraction, derived from about 400 g of whole cells, is resuspended in 1 liter of 0.05 M Tris-HCl, pH 7.5, by mixing at low speed. After the crude cell wall fraction is thoroughly resuspended in the Tris buffer, 50 mg of trypsin (pancreatic trypsin, Sigma Chemical Co., St. Louis, Mo.) are added and stirred using a magnetic stirring bar at room temperature for 6–24 hours. Following the trypsin treatment, 50 mg of pronase (*Streptomyces griseus* protease, Sigma Chemical Co., St. Louis, Mo.) are added to each liter of trypsin digested cell wall suspension. The suspension is stirred using a magnetic stirring bar for 6–24 hours at room temperature.

Example V

The protease digested cell wall fraction from Example IV is then treated with detergent and phenol. To each liter of cell wall suspension, 60 g of urea (J. T. Baker Chemical Co., Phillipsburg, N.J.), 2.0 ml of 100% Triton X100 (polyoxyethylene ethers, Sigma Chemical Co., St. Louis, Mo.), and 100 g of phenol crystals (Fisher Scientific, Fair Lawn, N.J.) are added. The flask containing the suspension is loosely covered with aluminum foil and warmed to 60°–80° C. and stirred for one hour. The deproteinized cell wall fraction is then spun for 10 minutes at 16,000× g in a GSA rotor (Ivan Sorvall, Inc., Norwalk, Conn.). The supernatant fraction is decanted and discarded and the dark fluid beneath the pellet is removed using a disposable pipette. The cell wall pellet is washed three times by resuspending it in about one liter of sterile water, and centrifuged at 16,000× g for 10 minutes in a GSA rotor.

Example VI

The washed, modified cell wall pellet is then lyophilized by transferring the suspension to a lyophilizing flask with a small amount of deionized sterile water. One 300 ml lyophilizing flask is used for each 30 grams of wet cell wall starting material. The cell wall suspension is shell frozen by rotating the flask in ethanol that had been cooled with solid carbon dioxide. After the content of the flask is frozen, the flask is attached to a lyophilization apparatus (Virtis Co., Inc., Gardiner, N.Y.). After the sample is lyophilized, it is transferred to a sterile, screw-cap container. The material is stored at −12° C. in a desiccator jar containing anhydrous calcium chloride.

Example VII

Several grams of lyophilized, deproteinized mycobacterial cell wall fraction are added to a dry, sterile, one liter beaker. Synthetic mineral oil, n-hexadecane (Drakeol 6-VR) is added at a concentration of 20 ml per gram and the mixture is covered and allowed to mix with stirring overnight. About 20 ml aliquots of the mycobacterial cell wall-oil mixture are transferred to sterile 1 liter beakers. Each 20 ml aliquot of mycobacterial cell wall fraction-oil mixture is diluted to 500 ml with PBS-D. Gentimicin is added to a final concentration of 30 µg per ml, amphotericin B is added to a final concentration of 2.5 µg per ml and thimersol is added to a final concentration of 0.01% The mixture is sonicated using a Heat Systems Sonicator XL2015 cell disruptor. All of the sonicated aliquot are combined, mixed thoroughly and microfluidized using a Microfluidics microfluidizer at 90–100 p.s.i. (20,700 to 23,000 p.s.i. actual chamber pressure). The micro fluidized emulsion is aliquoted into sterile Type I glass bottles under sterile laminar air flow sing a Filamatic Vial Filler (National Instrument Co., Baltimore, Md.). The vials are capped, sealed and stored at 4° C.

Example VIII

To test the effect of nonspecific immunostimulation on reproductive performance the following study is performed.

The composition of the immunostimulant emulsion is described in Example VI. The emulsion contains 1000 µg MCWE per ml.

In this study, 150 young American Dark Female minks weighing 800 g to 1000 g are divided into three equal groups and are subjected to the same animal husbandry management. All females in each of the three groups are mated on a given day to the same group of fertile mature males housed in the same shed.

Treatment A The 50 females in Group A receive 10 µg of MCWE in 10 µl of the immunostimulant emulsion intramuscularly 10 hours before mating.

Treatment B The 50 females in Group B receive 10 µg of MCWE in 10 µl of the immunostimulant emulsion intramuscularly eight days prior to mating and 10 µg of MCWE in 10 µl of the immunostimulant emulsion intramuscularly 12 hours before mating.

Treatment C The 50 females in Group C receive no treatment.

The following parameters of reproductive performance are evaluated:

Mating Rate=[mated females/total number in the group] X 100.

Pregnancy Rate=[females producing/mated females] X 100.

Litter Size=[total number of young born/females producing] X 100.

Survival Rate=[total number of young weaned/total number of young born] X 100.

Litter Size Weaned-[total number of young weaned/females producing] X 100.

Table 1 shows the results of treatments A, B and C on reproductive performance.

TABLE I

| Treatment* * | Mating Rate (%) | Pregnancy Rate*** (%) | Litter Size (Born) ± SEM | Survival Rate | Litter Size (Weaned) ± SEM |
|---|---|---|---|---|---|
| A | 90.0 (45/50) | 84.4 (38/45) | $5.87 \pm 0.34^{a*}$ | 98.2 (219/223) | $5.76 \pm 0.37^{a}$ |
| B | 90.0 (45/50) | 95.5 (43/45) | $5.56 \pm 0.30^{a}$ | 98.7 (236/239) | $5.49 \pm 0.30^{a}$ |
| C (Control) | 84.0 (42/50) | 90.5 (38/42) | $3.87 \pm 0.26^{b}$ | 97.9 (144/147) | $3.79 \pm 0.26^{b}$ |

$^{a, b}$values in the same column with different superscripts differ significantly ($p < 0.05$) or $p < 0.10$) Students T-test.
*Treatment:
A 10 µg IM 12 hours before mating.
B 10 µg IM on day −8 and second dose of 10 µg IM 12 hours before mating.
***"Pregnancy Rate" relates to the number of females mated producing live young.

Litter size born is significantly greater in experimental Groups A and B than in control Group C. The increased litter size in Groups A and B is maintained successfully throughout weaning and indicates that these young females are physiologically capable of nursing extra young during their first lactation. These results show the unexpected beneficial effect of nonspecific immunostimulation on reproductive performance.

Figure 1B:
Figure 1C:
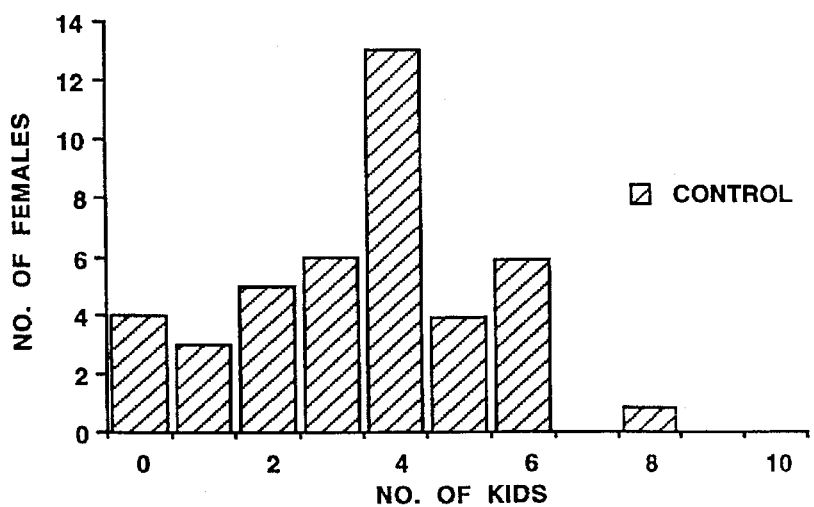

FIG. 1 shows the results of treatment A, B and C on the distribution of litter size born. Animals in Group B produce numerous large litters, not exceeding in any case 8 kittens. These results suggest that the primed immune system (Group B) provides a significantly better ($p<0.05$) reproductive performance response to MCWE treatment than does the unprimed immune system (Group A). However, both groups receiving MCWE (Group A and Group B) provide a better reproductive performance response to the MCWE treatment then does the untreated group (Group C).

Example IX

To further test the effect of nonspecific immunostimulation on reproductive performance the following study is performed.

The composition of the immunostimulant emulsion for use in this study is described in Example VIII. The emulsion contains 2000 µg MCWE per ml.

In this study, 12 mares of breeding age, each having a history of poor reproductive performance, are divided into two groups and subjected to the same animal husbandry.

Treatment A The 6 females in Group A receive 1500 µg of MCWE in 750 µl of the immunostimulant emulsion intravenously at heat and are bred to males of proven fertility at the second subsequent heat.

Treatment B The 6 females in Group B receive no treatment at heat and are bred to males of proven fertility at the second subsequent heat.

Results Two months later, 75% of the mares in Treatment Group A are in foal, whereas 30% of the mares in Treatment Group B are in foal.

These results show the unexpected beneficial effect of nonspecific immunostimulation on reproductive performance.

It should be understood, of course, that the foregoing relates only to preferred embodiments of the present invention and that numerous modifications or alterations may be made therein without departing from the spirit and the scope of the invention as set forth in the appended claims.

We claim:

1. A method of increasing reproductive performance in a human or animal comprising administering to the human or animal an amount of a nonspecific immunostimulant prepared from a bacterial cell wall extract effective to increase the reproductive performance of the human or animal, wherein the bacterial cell wall extract is administered prior to ovulation.

2. The method of claim 1 wherein the bacterial cell wall extract is prepared from Mycobacteriacae.

3. The method of claim 2, wherein the bacterial cell wall extract is prepared from Mycobacteria.

4. The method of claim 3, wherein the bacterial cell wall extract is prepared from *Mycobacterium phlei*.

5. The method of claim 1, wherein the cell wall extract is deproteinized.

* * * * *